United States Patent [19]

Lover et al.

[11] 4,128,662

[45] Dec. 5, 1978

[54] GLYCINE TOXICANTS

[75] Inventors: Myron J. Lover, Mountainside; Arnold J. Singer, South Orange; Donald M. Lynch, Waldwick; William E. Rhodes, III, Roselle, all of N.J.

[73] Assignee: Block Drug Company, Inc., Kenilworth, N.J.

[21] Appl. No.: 791,780

[22] Filed: Apr. 28, 1977

[51] Int. Cl.$^2$ .............................................. A01N 9/20
[52] U.S. Cl. ................................................... 424/319
[58] Field of Search ......................................... 424/319

[56] References Cited

U.S. PATENT DOCUMENTS

| 2,890,960 | 6/1959 | Dvorkovitz et al. ............ 424/319 X |
| 3,947,589 | 3/1976 | Misato et al. ........................ 424/319 |

*Primary Examiner*—Allen J. Robinson
*Attorney, Agent, or Firm*—Ostrolenk, Faber, Gerb & Soffen

[57] ABSTRACT

Certain substituted glycine compounds have been found to exhibit strong ovicidal activity, with a good degree of insecticidal activity.

6 Claims, No Drawings

GLYCINE TOXICANTS

BACKGROUND OF THE INVENTION

Many species of insects encase their ova in protective sheaths which are impregnable to most toxicants. The gestation period of the egg is often relatively long in comparison to the life cycle of the adult forms. Thus, an agent effective only against adults must persist for the lifetime of the developing ovum, or must be re-applied as successive hatchings occur.

Highly effective insect ovicides having low toxicity to mammals are quite rare.

It has now been found that certain N-acyl sarcosines, i.e., N-acyl-N-methyl glycines, exhibit effective ovicidal activity, often with a useful degree of insecticidal activity. These glycines are well known as surface active agents and have been incorporated in many pharmaceutical and cosmetic preparations as such. For example, tetradecylamine lauroyl sarcosinate has been used in an anti-dandruff preparation and cocoyl sarcosine constitutes greater than 10% of Head and Shoulders shampoo. Cocoyl sarcosine has been used in hair tint shampoos at a pH of 5.5. Dvorokovitz (U.S. Pat. No. 2,890,960) teaches the use of antienzymes including lauryl sarcosinic acid to retard ovideposition in fruit flies.

It is the object of this invention to provide new safe and effective toxicants for insects and their ova. The low mammalian toxicity of the subject compositions and methods renders them especially suitable for the treatment of ectoparasitic diseases, such as lice and scabies, in man and animals. In these applications, the ovicidal properties are particularly noteworthy, both for speed of impact and for potency. This and other objects of the invention will become apparent to those skilled in the art from the following detailed description.

SUMMARY OF THE INVENTION

This invention relates to ovicides and insecticides and the method of controlling insects. More particularly, the invention relates to the use of certain N-acyl-N-methyl glycines as toxicants for ectoparasites and their ova and to toxicant compositions containing such glycines.

DESCRIPTION OF THE PREFERRED EMBODIMENTS

The toxicants of the instant invention are those N-acyl-N-methyl glycines in which the acyl moiety contains 12 to 20 carbon atoms, preferably 13 to 20 carbon atoms. Typical examples of the glycines are lauroyl sarcosine (N-lauroyl-N-methyl glycine), oleoyl sarcosine (N-oleoyl-N-methyl glycine) and cocoyl sarcosine (N-cocoyl-N-methyl glycine) and the like.

As noted earlier, the glycines of the instant invention are known compounds and have been used as surface active agents in shampoo formulations. Shampoo formulations generally have pHs in excess of 5.5. It has been observed that only the acid form of the sarcosine is active and therefore the pH of the formulation containing the sarcosine must be less than 5.5 for the material to exhibit optimum pediculicidal and ovicidal activity. Accordingly, the prior art shampoos employed the sarcosine as a surfactant in the form in which they were not toxicant, except to the limited extent that the acidic form may have existed in equilibrium with the ionized salt.

One or more of the toxic glycines of the present invention can be incorporated into an active toxicant composition which can be in the form of a liquid, powder, lotion, cream, gel or aerosol spray, or foam as the result of formulation with inert pharmaceutically acceptable carriers by procedures well known in the art. Any pharmaceutically acceptable carrier, whether aqueous or not aqueous, which is inert to the active ingredient can be employed. By inert is meant that the carrier does not have a substantial detrimental effect on the pediculicidal or ovicidal toxicant performance of the active ingredient.

The active glycines are incorporated into the toxicant composition used to treat the substrate (human or animal) in need of such treatment, believed to be in need of such treatment, or desired to be prophylactically protected in an effective toxicant amount. By such amount is meant the amount which will cause at least 50%, preferably at least 75%, of the ectoparasites exposed in the two minute immersion tests described below to die within 24 hours in the case of lice and within 2 weeks in the case of the ova. The minimum concentration of glycines in the composition required to provide an effective toxic amount varies considerably depending on the particular glycine, the particular inert pharmaceutically acceptable carrier being employed and any other ingredients which are present. Thus, in one case a 5% concentration may suffice, while in other cases, concentrations as high as 30 to 40% may be required to obtain an effective toxic dose. In most instances, however, a concentration of 1 to 15% is sufficient. Higher concentrations may be irritating to the skin or eyes of vertebrates.

The instant glycines can also be employed as an adjunct toxicant in a preparation which otherwise exhibits pediculicidal and/or ovicidal activity. In such preparations, the term "effective toxic dose" means that amount which will increase the mortality rate by at least about 20% in the standard immersion tests.

The formulation in which the glycine is used must have a pH below about 5.5. It is preferred to maintain the pH above about 2.0 and the preferred pH range is about 3 to 5. The pH can be adjusted by procedures well known in the art, e.g., by using a suitable acid, ion exchange resins, etc.

The two minute immersion test referred to above is carried out as follows:

Pediculicidal activity: A 50 ml beaker is filled with tap water and allowed to come to room temperature (about 24° C.). Ten young adult male and ten young adult female lice (*Pediculus humanus corporis*) of the same age group and from the same stock colony are placed on a 2 × 2 cm coarse mesh patch. The sample to be tested, maintained at room temperature, is shaken until homogeneous and placed into a 50 ml beaker. The mesh patch is placed into the sample immediately after pouring, allowed to submerge, and after two minutes is removed and immediately plunged into the beaker containing the tap water. The patch is vigorously agitated every ten seconds and after one minute the patch is removed and placed on paper toweling. The lice are then transferred to a 4 × 4 cm black corduroy cloth patch and this point of time is considered zero hours. Thereafter, the corduroy patch is placed in a petri dish which is covered and stored in a 30° C. holding chamber.

Ovicidal activity: 15 adult, 5 to 10 day old, female lice (*Pediculus humanus corporis*) are placed on a 2 × 2 cm nylon mesh patch which is placed in a petri dish, covered and maintained in an incubator at 30° C. for 24 hours. The adult lice are then removed and the number of plump, viable eggs and shriveled non-fertile eggs on the patch are recorded. The sample to be tested, maintained at room temperature, is shaken until homogeneous and poured into a 50 ml beaker. Immediately after the pouring, the mesh patch is placed into the beaker, allowed to submerge, and after two minutes is removed and immediately plunged into a 50 ml beaker containing tap water at room temperature (about 24° C.). The patch is vigorously agitated every ten seconds and after one minute, the patch is removed and placed on paper toweling for one minute. The patch is then placed in a petri dish which is covered and stored in the 30° C. incubator. Fourteen days following treatment, the number of hatched eggs and the number of shriveled or unhatched eggs is noted.

In both the pediculicidal and ovicidal two minute immersion test, controls are run in identical manners to that described with room temperature (24° C.) tap water substituted for the sample to be tested. The results of the tests reported are net results.

In the following tables 1 and 2, the results of pediculicidal and ovicidal testing of lauroyl sarcosine is set forth. The sarcosine was tested at various concentrations in a formulation which contained 25% isopropanol and water q.s. ad. 100%.

Table 1

| | Pediculicidal Activity | |
|---|---|---|
| | Concentration. % | Mortality, % |
| Acid | | |
| | 1 | 0 |
| | 2 | 5 |
| | 3 | 5 |
| | 4 | 5 |
| | 5 | 20 |
| | 6 | 75 |
| | 7 | 90 |
| | 8 | 100 |
| Sodium Salt | | |
| | 30 | 5 |
| | 40 | 0 |
| | 50 | 5 |
| | 60 | 5 |
| | 70 | 5 |
| | 80* | 0 |
| | 90* | 0 |

*isopropanol level was zero in these samples.

Table 2

| | Ovicidal Activity | |
|---|---|---|
| | Concentration, % | Mortality, % |
| Acid | | |
| | 1 | 82 |
| | 2 | 62 |
| | 3 | 96 |
| | 4 | 100 |
| | 5 | 100 |
| | 6 | 100 |
| | 7 | 100 |
| | 8 | 100 |
| | 9 | 100 |
| | 10 | 100 |
| Sodium Salt | | |
| | 30 | 0 |
| | 40 | 20 |
| | 50 | 12 |
| | 60 | 38 |
| | 70 | 0 |
| | 80* | 34 |
| | 90* | 77 |

*isopropanol level was zero in these samples.

Tables 1 and 2 illustrate that when the sarcosine is used in the form of sodium salt, i.e., at an approximately neutral pH, the formulations are not strongly pediculicidal or ovicidal.

The pediculicidal and ovicidal activity of oleoyl sarcosine as a function of concentration was determined in a formulation which contained 25% isopropanol and water q.s. ad. 100%. The results are shown in table 3.

Table 3

| | Mortality, % | |
|---|---|---|
| Concentration, % | Pediculicidal | Ovicidal |
| 1 | 40 | 77 |
| 2 | 75 | 100 |
| 3 | 75 | 100 |
| 4 | 55 | 100 |
| 5 | 65 | 100 |
| 6 | 100 | 100 |
| 7 | 95 | 100 |
| 8 | 100 | 100 |

The pediculicidal and ovicidal activity of cocoyl sarcosine was determined as a function of concentration in a system containing 25% isopropanol and water q.s. ad. 100%. The results are shown in Table 4.

Table 4

| | Mortality, % | |
|---|---|---|
| Concentration, % | Pediculicidal | Ovicidal |
| 1 | 5 | 100 |
| 2 | 5 | 93 |
| 3 | 15 | 100 |
| 4 | 10 | 100 |
| 5 | 35 | 100 |
| 6 | 50 | 100 |
| 7 | 40 | 100 |
| 8 | 40 | 100 |
| 9 | 75 | 100 |
| 10 | 80 | 100 |
| 12 | 70 | — |
| 15 | 100 | — |

The sarcosines may be used in formulations other than those used to determine the data set forth in the foregoing tables. For example, a composition containing 50% stearoyl sarcosine and 50% ethanol has an activity of 80% in the standard ovicidal testing described before. Similarly, a formulation containing 15% stearoyl sarcoside, 25% isopropanol, 7% Tween 80 and 53% water exhibits 100% activity in both the pediculicidal and ovicidal tests hereinberfore described.

Some typical formulations are set forth below and the amounts recited are percentages by weight:

| | |
|---|---|
| Clear liquid suitable for mechanical spray application or inunction | |
| isopropanol | 40 |
| lauroyl sarcosine | 10 |
| water | 60 |
| Clear liquid shampoo | |
| isopropanol | 25 |
| cocoyl sarcosine | 4 |
| triethanolamine lauryl sulfate | 20 |
| water | 51 |
| Powder | |
| pyrophyllite | 94 |
| oleoyl sarcosine | 6 |
| Quick breaking aerosol foam | |
| mono and diglycerides from the glycerides of edible fats | 8 |
| isopropanol | 25 |
| lauroyl sarcosine | 8 |
| glycerin | 3 |
| water | 48 |
| isobutane | 8 |
| Ovicidal aerosol spray | |
| cocoyl sarcosine | 1 |
| isopropanol | 25 |
| water | 64 |

-continued

| | |
|---|---|
| isobutane | 10 |
| Ovicidal liquid suitable for mechanical spray application or inunction | |
| oleoyl sarcosine | 2 |
| isopropanol | 35 |
| water | 63 |
| Gel | |
| isopropanol | 25 |
| oleoyl sarcosine | 7 |
| xanthan gum | 2 |
| acetic acid, 1N | 10 |
| water | 56 |
| Cream | |
| cetyl alcohol | 3.0 |
| cocyl sarcosine | 14.0 |
| glyceryl monostearate | 8.0 |
| sorbitan monostearate | 8.0 |
| isopropanol | 25.0 |
| xanthan gum | 0.3 |
| water | 41.7 |

The ovicidal aerosol spray and the ovicidal liquid are primarily ovicidal; all other formulations are both insecticidal and ovicidal.

Various changes and modifications can be made in the instant invention without departing from the spirit and scope thereof. The various embodiments disclosed herein were for the purpose of further illustrating the invention but were not intended to limit it. Throughout this specification and claims, all temperatures are in degrees Centigrade and all parts and percentages are by weight unless otherwise indicated.

We claim:

1. A method of controlling insects or their ova which comprises applying to a human or animal in need of such control an effective toxic amount of at least one N-$C_{12-24}$ aliphatic acyl-N-methyl glycine.

2. The method of claim 1 wherein said acyl moiety contains 13 to 20 carbon atoms.

3. The method of claim 2 wherein said acyl moiety is selected from the group consisting of lauroyl, oleoyl, cocoyl and stearoyl.

4. The method of claim 1 wherein said glycine is employed in combination with an inert pharmaceutically acceptable carrier.

5. The method of claim 4 wherein said carrier is an aqueous carrier.

6. The method of claim 4 wherein said combination has a pH of less than 5.5.

* * * * *